United States Patent [19]
Remaley et al.

[11] Patent Number: 6,154,706
[45] Date of Patent: Nov. 28, 2000

[54] APPARATUS AND METHOD FOR KINETIC ANALYSIS OF THE INTRAOPERATIVE ASSAY FOR PARATHYROID HORMONE

[76] Inventors: Alan T. Remaley, 4510 Traymore St., Bethesda, Md. 20814; Mark Ruddel, 12019 Veris Mill Rd., Apt. 301, Wheaton, Md. 20906; Phillip C. Miller, 32402 Crete Rd., Dana Point, Calif. 92626

[21] Appl. No.: 09/289,157

[22] Filed: Apr. 9, 1999

[51] Int. Cl.[7] .......................... G01N 33/48; G01N 33/50; G01N 33/53; G01N 33/546
[52] U.S. Cl. ............................ 702/19; 436/500; 436/527; 436/536; 436/518; 435/7.1; 424/1.24
[58] Field of Search ........................... 702/19.1; 436/500, 436/527, 536, 518; 435/7.1; 424/1.24

[56] References Cited

PUBLICATIONS

Arnold, L, et al, "Automated Immunoassay Systems", Laboratory Instrumentation, Haven, M, et al, eds, Chap 19, 1995, pp 347–352.

Duquenne, M., et al, "Serum parathormone profile during surgical treatment of hyperfunctioning parathyroid adeonoma: a multicompartment model", J Bone and Mineral Res, vol. 9, No. 9, 1994.

Greenblatt, D., Koch–Weser, J. Clinical Pharmocokinetics, Part I, New England Journal of Medicine, vol. 293, No. 14, Oct. 2, 1975 pp 702–5.

Greenbalt, D., Koch–Weser, J, Clinical Pharmocokinetics, Part II, New England Journal of Medicine, vol. 293, No. 19, Nov. 6, 1975, pp 964–970.

*Primary Examiner*—John S. Brusca
*Assistant Examiner*—Stephen Siu
*Attorney, Agent, or Firm*—Stout, Uxa, Buyan & Mullins, LLP; Donald E. Stout

[57] ABSTRACT

An apparatus for predicting a residual hormone concentration in a patient after a removal of a portion of the patient's glandular tissue which secretes the hormone, includes an input device constructed to receive a plurality of measured hormone concentrations corresponding to a plurality of human fluid samples taken from a patient at a plurality of sample times, respectively; and further includes a computer processor configured to iteratively calculate a residual hormone concentration. In accordance with one feature of the present invention, the computer processor is configured to generate data denoting a residual amount of glandular tissue that will remain in the patient after the removal of the portion of the patient's glandular tissue; and the apparatus further comprises an output device constructed to output the generated data denoting the residual amount of glandular tissue. The computer processor is further configured to iteratively calculate a half-life value of the hormone concentration in the patient.

78 Claims, 4 Drawing Sheets

APPARATUS AND METHOD FOR KINETIC ANALYSIS OF THE INTRAOPERATIVE ASSAY FOR PARATHYROID HORMONE

BACKGROUND OF THE INVENTION

1. Field of the Invention

The present invention relates generally to medical devices and procedures and, more particularly, to apparatuses and methods for predicting hormone levels in patients after removal of portions of hormone-secreting glands.

2. Description of Related Art

Primary hyperparathyroidism, which is the result of the hypersecretion of parathyroid hormone (PTH) by abnormal parathyroid glands, is relatively common, with an overall incidence of approximately 1 in 1000. The incidence of disease increases with age and is more common in women. Secondary hyperparathyroidism is also the result of excess parathyroid hormone production. The parathyroid hormone secretion, however, is appropriate in secondary hyperparathyroidism and is in response to low serum calcium, as a consequence, for example, of chronic renal disease. Familial hypocalciuric hypercalcemia is an autosomal dominant genetic disorder, and it is important to recognize because these patients do not benefit from parathyroidectomy. The genetic defect is in the calcium receptor, which makes it less sensitive to calcium and consequently leads to increased parathyroid hormone secretion. The other causes of hypercalcemia include various diet and drug induced causes, as well as several miscellaneous endocrine and inflammatory disorders.

Most of the symptoms are predictable based on the known function of parathyroid hormone. The excess parathyroid hormone causes accelerated bone loss, which can lead to bone demineralization and pathologic bone fractures. Kidney stones are another common manifestation of the disease. Although parathyroid hormone increases the renal reabsorption of calcium from urine, the overall urinary excretion of calcium is still increased because of the elevated serum calcium. Excess calcium in the urine can form a complex with phosphate and form kidney stones. In addition to these predicted manifestations, there are also numerous vague constitutional symptoms, such as gastrointestinal discomfort, and various mental status changes, such as depression and anxiety. In the past, most patients were not diagnosed until they presented signs and symptoms. Since the advent of chemistry screening panels, the majority of patients are now diagnosed earlier in their disease by an elevated serum calcium and are often asymptomatic.

The parathyroid glands are pea size glands located posterior to the thyroid gland. Typically there are 4 glands, but approximately 2 to 6% of individuals have more than 4 glands, and sometimes as many as 12 glands. Parathyroid glands can also be located in atypical or ectopic locations in about 15% of patients. Embryologically the parathyroid glands are derived from tissue in the upper part of the neck that later descends to their adult locations. Ectopic glands can be found anywhere from behind the ear to all the way in to the chest, for those glands that have over migrated. Approximately in 80–85% of cases, primary hyperparathyroidism is caused by a solitary benign parathyroid adenoma. Parathyroid adenomas are a clonal expansion of a cell that has an altered set point for regulating calcium that results in the over production of parathyroid hormone relative to the level of serum calcium. Less than 1% of parathyroid adenomas are malignant. The remaining cases of hyperparathyroidism are caused by multiple adenomas (2–3%) or by a diffuse enlargement or hyperplasia of all of the parathyroid glands (12–15%). The hyperplasia of parathyroid glands is often associated with Multiple Endocrine Neoplasia, a genetic disorder that is characterized by adenomas in multiple endocrine glands, such as the pituitary, parathyroid, adrenal and pancreas.

The overproduction of parathyroid hormone, which is synthesized by the parathyroid gland and is the key hormone that regulates calcium metabolism, is a relatively common disease referred to as hyperparathyroidism. Adenomas of the parathyroid gland often cause the overproduction of parathyroid hormone. The elevated serum calcium caused by the excess parathyroid hormone can result in various constitutional symptoms and can account for the formation of kidney stones and the loss of bone density in patients with hyperparathyroidism. The treatment of choice for hyperparathyroidism is surgical removal of any parathyroid adenomas.

There are approximately 180,000 parathyroidectomies performed annually worldwide. The goal of the surgery is the complete removal of the parathyroid hormone hypersecreting glands. Patients with solitary adenomas are cured after the removal of the one abnormal gland. Patients with diffuse hyperplasia of 4 glands are usually treated by the excision of approximately 3.5 glands. Residual tissue is left behind to prevent the development of hypocalcemia. The main challenge in the surgical treatment of hyperparathyroidism is the identification of the parathyroid glands that are over producing parathyroid hormone.

Recent radiologic techniques have improved the preoperative localization of adenomas, but they are not fully reliable. During surgery, the direct visual inspection of the size and color of the gland can also be helpful, but it is not fully reliable for identifying abnormal parathyroid glands. Histologic examination, at the time of surgery, of any excised tissue is usually helpful for distinguishing normal from abnormal parathyroid glands. Parathyroid adenomas, however, can not be readily distinguished from hyperplasia by histology. This is an important limitation, because even if the removed gland is found to be abnormal, one can not exclude the possibility that the remaining glands are hyperplastic. In addition, patients with parathyroid adenomas that have multiple adenomas can be missed by performing just a histologic exam of 1 gland. Because of these problems, all 4 glands are usually inspected grossly during surgery and often biopsied for histologic examination. This increases the time and expense of the surgery and also increases the chance for morbidity from the procedure, the most important of which is damage to the recurrent laryngeal nerve and subsequent vocal cord dysfunction. Despite the extra precaution of inspecting all the parathyroid glands, as many as 10–15% of patients, depending on the experience of the surgeon, are not cured the first time by surgery. Treatment failures occur, in part, because of the difficulty in identifying and recognizing abnormal glands, and because of ectopic and supernumerary parathyroid glands.

In performing surgical procedures for excising parathyroid adenomas, surgeons need to be able to quickly determine whether all of the parathyroid adenomas have been removed. Because all of the signs and symptoms of hyperparathyroidism are the result of excess parathyroid hormone, the intraoperative monitoring of the drop in serum parathyroid hormone following the excision of abnormal parathyroid glands can be used to confirm the removal of the parathyroid adenoma.

One device for facilitating monitoring of the drop in serum parathyroid hormone is an intraoperative assay for the quantitative determination of parathyroid hormone levels, referred to as the QuiCk-IntraOperative™ Intact PTH, and developed and sold by Nichols Institute Diagnostics of San Juan Capistrano, Calif. By facilitating the determination of parathyroid hormone levels in human serum and Ethylenediaminetetraacetic Acid (EDTA) treated samples, the intraoperative assay provides the surgeon with a means for quickly determining whether all of the parathyroid adenomas have been removed. Another similar product is the Nichols Advantage® Chemiluminescence Specialty System, also sold by Nichols Institute Diagnostics and described, for example, at http://www.nicholsdiag.com.

Since the half-life of parathyroid hormone is approximately 3 minutes, the removal of the abnormal gland can be assessed by a drop of serum parathyroid hormone within 5 to 10 minutes after the resection of the tissue. Because the secretion of parathyroid hormone by the remaining normal glands are suppressed by the elevated serum calcium, the level of parathyroid hormone quickly drops into either the normal or below normal range after the surgery. The intraoperative assay is used to detect whether the parathyroid hormone concentration has decreased by more than 50% within 5 minutes post resection, indicating that the patient is cured. A primary means of intraoperatively determining whether a complete surgical removal of multiple parathyroid adenomas, for example, has occurred has been the measurement of the drop in serum parathyroid hormone. The prior art to Applicants' knowledge has proposed no other satisfactory means for intraoperatively confirming the surgical removal of parathyroid adenomas.

The conventional intraoperative assay, which requires the measurement of the parathyroid hormone concentration at 5 minutes post resection, can be extremely time-restrictive. The choice of the 5 minute time point is arbitrary, but the value for interpreting the result is only valid for the 5 minute time point. The requirements of surgery can render collection of the serum at precisely the 5 minute time point difficult. The prior-art intraoperative assay does not provide recommendations on how to interpret the data when the serum is collected earlier or later than the 5 minute time point.

Moreover, the half-life of the decay of the parathyroid hormone in patients can vary as much as five-fold, which if not accounted for can significantly affect the interpretation of the data and can potentially lead to false positive and false negative diagnoses. It can be difficult using the prior-art intraoperative assay to directly translate the percent drop in parathyroid hormone into how much residual parathyroid hormone secreting tissue is present after the surgery. In addition, it can be difficult to translate the percent drop in parathyroid hormone at 5 minutes to the expected level of PTH when it reaches equilibrium. Both of these concerns can be particularly important, for example, in patients with multiple adenomas/hyperplasia. If the parathyroid hormone result is not correctly interpreted, incomplete removal of the adenomas or excess removal of parathyroid tissue can occur.

SUMMARY OF THE INVENTION

The apparatus and method of the present invention allow for kinetic analysis and prediction of both parathyroid hormone levels and remaining parathyroid hormone-secreting tissue. The kinetic analysis of the present invention is not dependent on any particular time point. Accordingly, surgeons are free to interpret the parathyroid hormone result at times deemed convenient to the surgeons, and surgeons missing the 5 minute time point are still able to interpret the parathyroid hormone result. An additional advantage of the present invention is that surgeons can perform collections at earlier time points, which can save time and money, and which can potentially lead to earlier determinations of the success of the surgery.

The kinetic-analysis apparatus and method of the present invention further facilitate the calculation of the half-life of parathyroid hormone for each individual patient, thus improving the reliability of the interpretation results. One feature of the present invention provides a prediction of the concentration of parathyroid hormone that will be present in the patient at equilibrium. The data is expressed as percent drop of parathyroid hormone from the baseline. In accordance with another aspect of the present invention, the data is expressed as residual parathyroid hormone secreting tissue, which may be more intuitive in assisting the surgeon in interpreting the results. Reporting the result as both percent drop of parathyroid hormone from baseline and as residual parathyroid hormone secreting tissue may improve the interpretation of the parathyroid hormone result and eliminate or attenuate under and over treatment of patients during surgery.

In accordance with one aspect of the present invention, an apparatus for predicting a residual hormone concentration in a patient after a removal of a portion of the patient's glandular tissue which secretes the hormone, includes an input device constructed to receive a plurality of measured hormone concentrations corresponding to a plurality of human fluid samples taken from a patient at a plurality of sample times, respectively; and further includes a computer processor configured to iteratively calculate a residual hormone concentration. In accordance with one feature of the present invention, the computer processor is configured to generate data denoting a residual amount of glandular tissue that will remain in the patient after the removal of the portion of the patient's glandular tissue; and the apparatus further comprises an output device constructed to output the generated data denoting the residual amount of glandular tissue. The computer processor is further configured to iteratively calculate a half-life value of the hormone concentration in the patient.

The input device can be constructed to receive a plurality of measured concentrations of parathyroid hormone (PTH). The apparatus and the computer processor can be constructed and configured to automatically determine the plurality of measured hormone concentrations from the plurality of fluid samples. These plurality of fluid samples can be drawn from one or more fluid compartments, wherein the term "fluid compartment(s)" refers to any type of human body fluid unless it is otherwise specified. For example, the human plasma is referred to as the plasma compartment. Each fluid sample in accordance with one aspect of the present invention includes, but is not limited to, Ethylenediaminetetraacetic Acid (EDTA) treated human plasma, serum, whole blood (as opposed to plasma or serum), saliva, cerebral spinal fluid, urine, amniotic fluid, tears, perspiration.

The computer processor of the apparatus is configured, in accordance with another feature of the present invention, to generate information relating to a decay curve of the hormone concentration of the patient, and is further configured to instruct the output device to output a graphical display of a decay curve of the hormone concentration of the patient.

In accordance with another aspect of the present invention, a method of using a computer processor to predict a residual hormone concentration in a patient after a removal of a portion of the patient's glandular tissue which secretes the hormone, comprises the steps of: (a) providing first (baseline-preoperative value), and post-excision second and third measured hormone concentrations corresponding to first, second and third human fluid samples taken from a patient at first, second and third sample times, respectively; and (b) assigning an estimated value to the residual hormone concentration of the patient that is to be predicted. The method includes the additional steps of: (c) determining an expression in half lifes of the second sample time, using the estimated value; (d) determining an expression in half lifes of the third sample time given the determined expression in half lifes of the second sample time and a ratio of the third sample time and the second sample time; (e) determining a hormone concentration that would remain at the third sample time if the residual hormone concentration were zero, using the determined expression in half lifes of the third sample time; and (f) calculating a difference between the determined hormone concentration and the third measured hormone concentration. The estimated value for the residual hormone concentration is remembered as an old estimated value at step (g), and a new estimated value is found for the residual hormone concentration, using the calculated difference at step (h). Steps (c) through (h) are repeated until a difference or percent change between the old estimated value and the new estimated value reaches a predetermined value.

The new estimated value is output as the predicted residual hormone concentration in accordance with one feature of the present invention, and data representing a residual amount of glandular tissue that remains in the patient after the removal of the portion of the glandular tissue is output in accordance with another feature of the present invention.

One broad aspect of the present invention is directed to a method of using a computer processor to predict a residual hormone concentration wherein the method has a first step of providing a plurality of measured hormone concentrations corresponding to a plurality of human fluid samples taken from a patient at a plurality of sample times, respectively; and further has a second step of iteratively calculating a residual hormone concentration.

The present invention, together with additional features and advantages thereof, may best be understood by reference to the following description taken in connection with the accompanying illustrative drawings.

DETAILED DESCRIPTION OF THE PRESENTLY PREFERRED EMBODIMENTS

Figure 1:
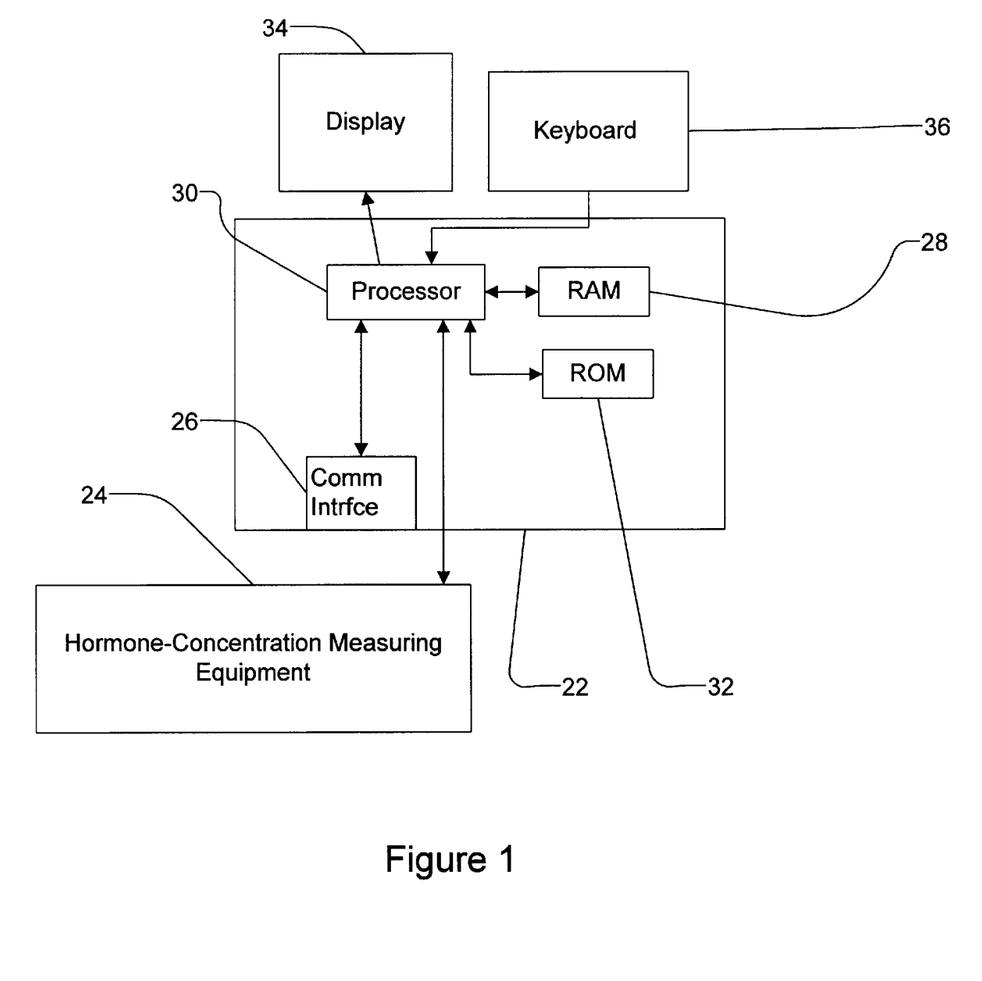
FIG. 1 is a general block diagram of a computer processor system in accordance with the present invention.

Referring now more particularly to the drawings, FIG. 1 illustrates a block diagram of a computer system 22 coupled to hormone-concentration measuring equipment 24, in accordance with the present invention. The computer system 22 comprises an optional communications interface 26, which may comprise, for example, a fax/modem and associated software. The computer system 22 includes a short term memory 28, which preferably comprises random access memory (RAM) and a computer processor 30 in which programs are stored and run, respectively, for controlling the functions of the computer system 22. The computer system 22 preferably also includes a long term memory 32, such as a read only memory (ROM) or electronically programmable read only memory (EPROM). The computer system 22 may also include a disk drive (not shown) for both long term and short term storage. The computer system 22 further includes a display 34 and a user input device 36, such as a keyboard. A system bus (not shown) interconnects the various components. Other components and busses (not shown) may be connected to the system bus for providing additional functionality and processing capabilities. The computer system 22 may be disposed within or adjacent to the hormone-concentration measuring equipment or, alternatively, the computer system 22 may be disposed remotely and may comprises a network access device for providing access to and from an Internet, Intranet, or other network system.

The hormone-concentration measuring equipment 24 comprises equipment for measuring hormone concentrations in human fluid samples. As presently embodied, the hormone-concentration measuring equipment 24 comprises an intraoperative assay system for the quantitative determination of parathyroid hormone levels, referred to above as the QuiCk-IntraOperative™ Intact PTH. As an alternative to the semi-manual QuiCk-IntraOperative™ Intact PTH system, the hormone-concentration measuring equipment 24 can comprise the above-mentioned Nichols Advantage Chemiluminescence Specialty System. Both systems facilitate the determination of parathyroid hormone levels in human serum and Ethylenediaminetetraacetic Acid (EDTA) treated samples.

The hormone-concentration measuring equipment 24, which as presently embodied comprises the QuiCk-IntraOperative™ Intact PTH system, is used to generate a particle immunoassay for intact plasma parathyroid hormone that utilizes a capture antibody immobilized to a polystyrene bead and a detector antibody coupled to an acridinium ester label. The assay is designed to accelerate the rate of reaction between the antibodies and parathyroid hormone by using high affinity antibodies, and by increasing the temperature and the rate of mixing during the assay. The antibody-parathyroid hormone complex is detected by chemiluminescence after the addition of a trigger solution, which causes the acridinium ester label to emit light.

The assay is semi-automated and as presently embodied is performed on a portable tube-luminometer work station produced by Nichols Institute Diagnostics. The work station has a small microcentrifuge for the rapid (30 second) separation of plasma from EDTA-anticoagulated blood. After the manual addition of the reagents and plasma into the reaction tube containing the polystyrene bead, the tube is incubated for 7 minutes at 40° C. and is rapidly mixed, using a vibrating heating block. Following the washing of the beads by an automatic tube washer, chemiluminescence is measured on a tube luminometer, which also performs all of the necessary calculations.

All the instrumentation for the assay is preferably situated on a cart that can be transported to the operating room. Performing the assay in the vicinity of the surgery is preferable in order to facilitate the rapid measurement and reporting of the result. Just prior to the surgery, a technologist runs a calibration curve in the central laboratory to save time and to identify any potential problems with the assay. The technologist then changes into surgical clothing and transports the cart with the instrumentation for the test into the operating room. Once the surgery is underway, a technologist is present to run the baseline and, for example, a 5 and 10 minute sample time point post excision of a gland.

Other sample time points, besides the 5 and 10 minute sample time points, may be used. For complicated cases, in which multiple suspected glands are removed, the technologist may return to the clinical laboratory until notified by phone or by page from the operating room, if additional analysis is necessary.

The above embodiment of the hormone-concentration measuring equipment is intended to be illustrative only. Other devices and methods for measuring parathyroid hormone levels or levels of other hormones, as would be known to one of ordinary skill in the art, directly are contemplated to be within the scope of the present invention. For example, the hormone-concentration measuring equipment 24 may in modified embodiments comprise devices, and methods for using same, for measuring ACTH, Calcitonin, Gastrin, Insulin and Cortisol. Hormones having substantially longer half lifes may also be amenable to the method of the present invention.

An advantage of using the method of the present invention with the hormone would be to estimate the number of half lifes of a hormone intraoperatively. An important element in accordance with an aspect of the present invention is that the hormone-concentration measuring equipment 24 facilitates the measuring of such hormone concentrations of a plurality of human fluid samples at a corresponding plurality of sample times. The hormone-concentration measuring equipment 24, in the presently preferred embodiment, facilitates the measuring of the hormone concentrations of three human fluid samples at three sample times.

Figure 2:
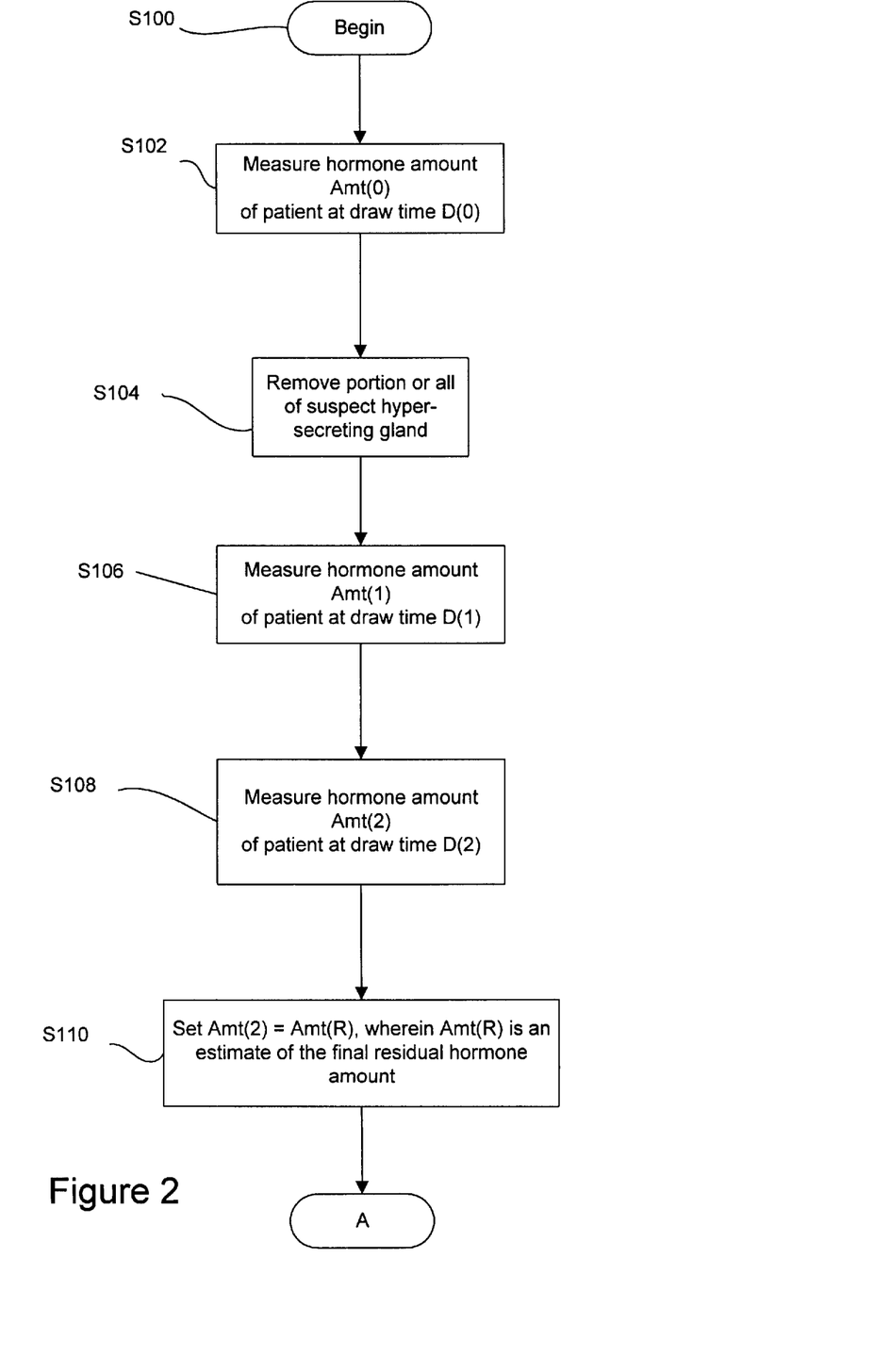
FIGS. 2–4 illustrate a flow chart of a method of the present invention.
Figure 3:
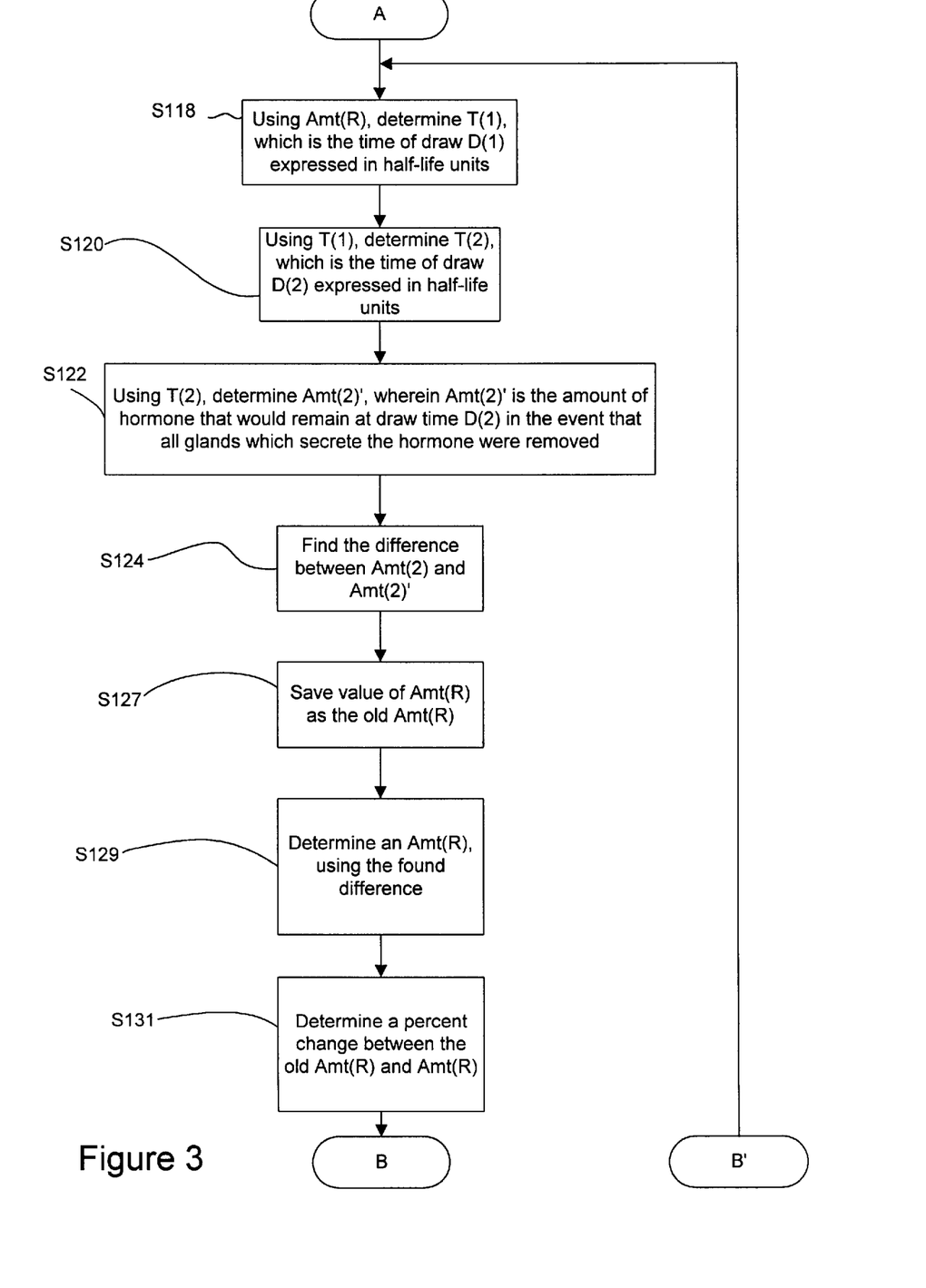
Figure 4:
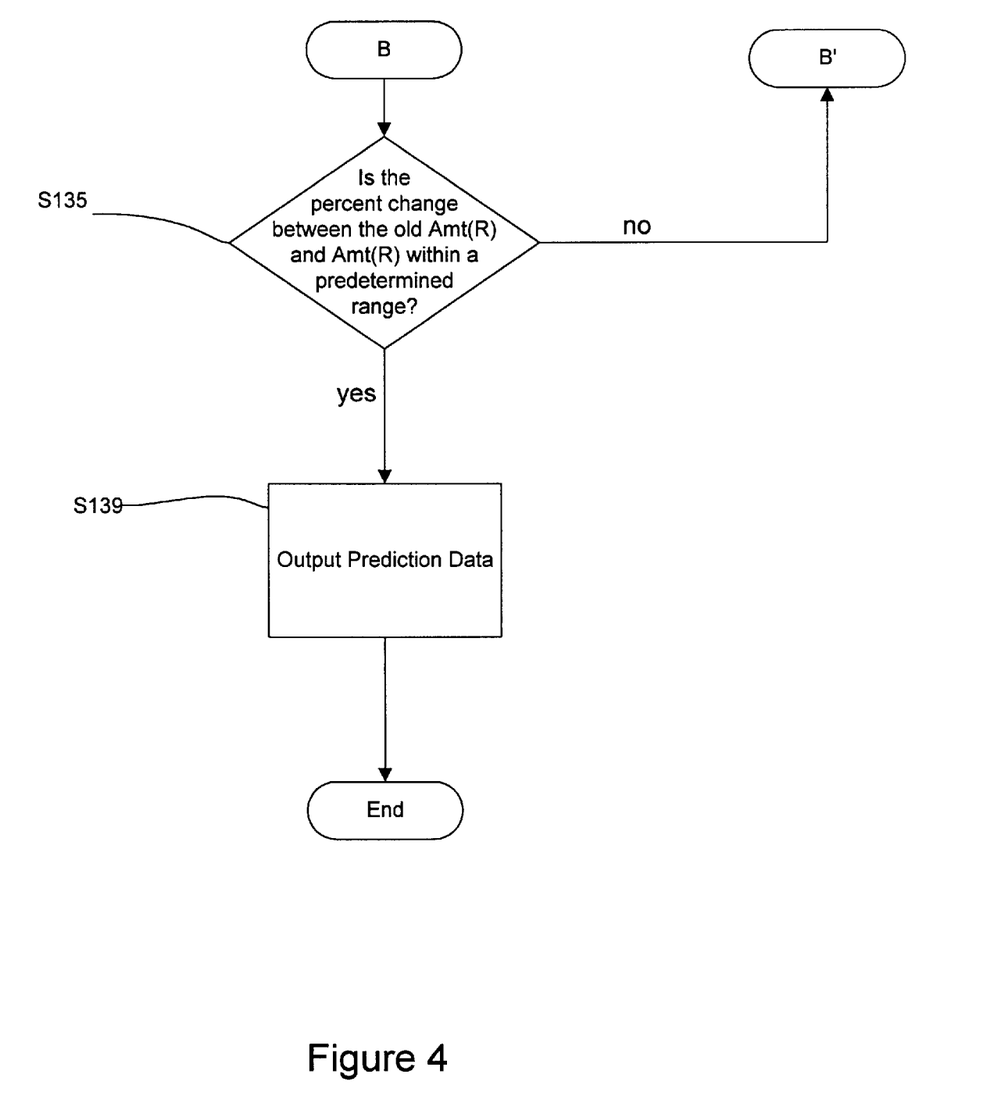

FIGS. 2–4 illustrate a flow chart of a method of the present invention. Many steps of the method of the present invention may be implemented in software or firmware, as well as in programmable gate array devices, an Application Specific Integrated Circuit (ASIC) or other hardware. In accordance with the presently preferred embodiment, the computer processor 30 executes software embedded instructions to implement much of the method illustrated in FIGS. 2–4.

In accordance with the method of the present invention, a number of human fluid samples are taken at different times, and the hormone concentrations are determined for each sample. The removal of a portion of a patient's hormone-secreting tissue will upset the equilibrium and the hormone concentration will drop until a new equilibrium is reached sometime later. The method of the present invention seeks to determine or predict the new equilibrium concentration.

When a portion of a hormone-secreting tissue (gland) is removed, the amount of hormone that was contributed by the gland disappears at a particular mathematical rate until all that is left is the amount being produced by the remaining glands. If no other glands remain, then the hormone concentration will be zero at equilibrium. Otherwise, the equilibrium concentration will be that produced by the remaining glands. In any event, the rate at which the hormone concentration declines is typically an exponential rate and can be expressed as corresponding to what are known as half lifes. For example, if the amount of hormone contributed originally by the gland to be excised is 40 and the half life is 1 minute, then the amount left from this gland at 1 minute is 20; at 2 minutes is 10; at 3 minutes is 5; at 4 minutes is 2.5; and so on. In other words, between any 2 points in time separated by a half life, the second point is ½ of the first point's value. Being able to express this mathematically, one can also find a concentration that is left from excision to any time after excision of the gland, such as, for example, 1.3 half lifes. As mentioned, when other glands not excised are still producing, the level will fall to the level produced by the other glands. For example, if the non-excised glands produce and continue to produce at the same level, say 30, in the above example at time 0, 1 half life, 2 half lifes and 3 half lifes, then the value would change from 70(40+30), 50(20+30), 40(10+30) and 35(5+30) with the concentration eventually leveling out at 30.

Referring to Table 1, an example is provided for illustrating a derivation of one of the equations implemented by the method of the present invention. If a patient has 1 abnormal gland that produces a level of 100 by itself and this is the only producing gland, then removal of this gland results in an eventual level of 0. The amount of hormone left is found by the equation:

$$\text{Amt}(X) = \text{Amt}(0) * (\tfrac{1}{2})^{T(X)} \qquad \text{Equation 1}$$

where Amt(X) is the amount of hormone concentration at time X, Amt(0) is the amount of hormone at time 0 and T(X) is the time of draw time X expressed in half lifes ($t_{1/2}$) or (HL). Equation 1 can be rewritten as follows:

$$\text{Amt}(X) = \text{Amt}(0) * 2^{-T(X)} \qquad \text{Equation 2}$$

In column 1 of Table 1, draw number 0 (D(0)) in row 1 is taken at 0 seconds, which is 0 half lifes and which as presently embodied is before the excision. Continuing in column 1, if the half life of the particular hormone for the particular patient is 5 seconds, then draw number 1(D(1)) in row 3 is taken at 5 seconds or 1 half life, and draw number 2 (D(2)) in row 5 is taken at 10 seconds or 2 half lifes. Although the present method works with only 3 draws of human fluid, column 1 of Table 1 actually shows 9 draws corresponding to rows 1–9. Accordingly, any 3 of these draws may be long as D(0) reflects the concentration (Amt (0)) of hormone at 0 seconds before the excision, in accordance with the presently preferred embodiment.

TABLE 1

| | 1<br>half<br>life | 2<br>amount left<br>of pth from<br>excised gland | 3<br><br><br>total | 4<br><br><br>expected | 5<br><br>diff<br>total - exp | 6<br><br>calculated<br>residual |
|---|---|---|---|---|---|---|
| 1 | 0 | 100.0 | 120.0 | 120.0 | 0.0 | |
| 2 | 0.5 | 70.7 | 90.7 | 84.9 | 5.9 | 20.0 |
| 3 | 1 | 50.0 | 70.0 | 60.0 | 10.0 | 20.0 |
| 4 | 1.5 | 35.4 | 55.4 | 42.4 | 12.9 | 20.0 |
| 5 | 2 | 25.0 | 45.0 | 30.0 | 15.0 | 20.0 |
| 6 | 2.5 | 17.7 | 37.7 | 21.2 | 16.5 | 20.0 |
| 7 | 3 | 12.5 | 32.5 | 15.0 | 17.5 | 20.0 |
| 8 | 3.5 | 8.8 | 28.8 | 10.6 | 18.2 | 20.0 |
| 9 | 4 | 6.3 | 26.3 | 7.5 | 18.8 | 20.0 |

It is noted that the times of the draws (D(X)) are expressed in time units, such as seconds, whereas the units in column 1 are expressed in half lifes. Accordingly, draw number 0 (D(0)) in row 1 of column 1 is expressed in half-life units as T(0)=0 half lifes; draw number 1 (D(1)) in row 3 of column 1 is expressed in half-life units as T(1)=1 half life; and draw number 2 (D(2)) in row 7 of column 1 is expressed in half-life units as T(2)=2 half lifes. To take another example, T(0.5) in row 2 would equal 0.5 half lifes which corresponds to a draw time of one minute if the half life were two minutes.

To review, column 1 is draw number times expressed in half-life units instead of minutes or seconds. Column 2 shows the amount of hormone left at the various draw number times, in a scenario where the initial hormone concentration is 100 and the final hormone concentration would eventually be zero. In this scenario shown in column 2, the concentration at 1 half life is half (50) of the initial concentration; the concentration at 2 half lifes is half (25) of the concentration at 1 half life; and so on. Column 3 illustrates a scenario wherein there is remaining hormone-secreting tissue after the excision of the tissue that originally secreted a concentration of 100. This other hormone-secreting tissue produces a concentration of 20 before the procedure, and throughout the procedure, since in this example the 20-unit secreting hormone is not affected. In column 3, when the 100-unit secreting gland is removed, the amount left that came from the removed gland will decrease the same way as in column 2, but with the 20-unit offset at all points. The non-excised hormone-secreting tissue seems to continue to produce approximately the same amount for some time after the levels fall and, subsequently, produces more after a day or so. Each value in column 3 corresponds to the value in column 2, with the 20-unit offset added, which accounts for the non-excised hormone-secreting tissue which remains after the excision. The hormone concentration in column 3 will eventually go down to 20, which is the residual amount.

In the example of Table 1, the residual amount is known (0 in column 2, 20 in column 3), but in actual surgical procedures this unknown variable is the one sought. The only known data in the actual surgical procedure will be 3 draw times and 3 hormone concentrations. In alternative embodiments, more than 3 draw time points and hormone concentrations may be used. Referring again to the starting value of 120 units of column 3, a surgeon initially excising tissue will not know before hand whether this initial value of 120 will drop to zero, indicating no residual tissue, or will drop to a residual amount, indicating residual hormone-secreting tissue. Column 4 shows the same decay curve as that of column 2, but with an initial concentration of 120 instead of 100. In other words, the numbers in column 4 correspond to an initial hormone concentration of 120 which decays to a value of 0, indicating a hypothetical scenario where there is no residual hormone secreting tissue.

Now, column 5 tabulates the differences between columns 3 and 4 for each draw number time. That is, for an initial hormone concentration of 120 units in this example, column 5 tabulates the difference for each draw number time between the scenario of column 3 where a residual amount of 20 units remains and the scenario of column 4 where no residual amount remains. At 1 half life the difference is 10 (7060); at 2 half lifes the difference is 15 (45–30); at 3 half lifes the difference 17.5 (32.5–15); and so on. This difference will continue to approach 20, the residual value in this example for column 3, as time goes on. The inventors have discovered that this difference, expressed in column 5, approaches the residual value (20) of column 3. At 1 half life it is ½ of 20, at 2half lifes it is ¾ of 20; at 3 half lifes it is ⅞ of 20; at 4 half lifes it is 15/16 of 20; and so on. It can be seen that the denominator is 2 to the power of the half lifes whereas the numerator is merely 1 less than that. An equation can be generated for the difference value of column 5, namely:

$$\text{Amt}(X)-\text{Amt}(X)'=\text{Amt}(R)*(2^{T(X)}-1)/(2_{T(X)}) \quad \text{Equation 3}$$

Where in this example, Amt(R) is equal to the amount of hormone concentration at the residual time or at equilibrium. The expression "Amt(X)–Amt(X)'" is the value in column 5; the expression "$2_{T(X)}-1$" is 2 to the draw number X expressed in half lifes, minus one; and the expression $2_{T(X)}$ is 2 to the draw number expressed in half lifes. In actual surgical situations, the difference between a measured hormone concentration at time X (assuming residual tissues) and a theoretical concentration that would occur at time X assuming no residual tissue, can be determined or approximated, but the actual residual concentration Amt(R) remaining at equilibrium, 20 in this example, is unknown. By simple rearrangement, the equation can be expressed as:

$$\text{Amt}(R)=[\text{Amt}(X)-\text{Amt}(X)']*2_{T(X)}/(2_{T(X)}-1) \quad \text{Equation 4}$$

Equation 4 would work by itself for determining the residual hormone concentration, if the rate of elimination were constant from patient to patient. In actuality, however, the biological half life varies considerably among patients. Accordingly, since the above expressions are in half-life time units, the equations are about as accurate as are the assumed or determined half lifes of the patients. Accordingly, both the half life of the patient as well as the predicted residual value must be determined. With both a linear term and an exponential term as unknowns, simple mathematical equations have not been found to be applicable. Thus, the present inventors have developed an iterative process for finding the curve that fits the data.

The algorithm of the present invention uses an estimate of the residual concentration, which as presently embodied comprises the hormone concentration of the third draw number, to calculate an estimate of the half life. The method then takes this half life and generates a better estimate of the residual concentration; takes this better estimate of the residual concentration to make a better estimate of the half life; and so on until the method reaches a predetermined criteria. As presently embodied, the predetermined criteria comprises a small change, preferably about 0.1 units between 2 successive iterations.

More particularly, as illustrated in the flow chart of FIGS. 2–4, the illustrated method comprises the following steps after beginning at step S100. At step S102 a hormone amount Amt(0) of the patient is drawn at draw time D(0), and at step S 104 a portion or all of the patient's hormone-secreting tissue is removed. Two subsequent hormone concentrations Amt(1) and Amt(2) are made at draw times D(1) and D(2), as shown in steps S106 and S108, respectively. At step S110, the hormone concentration at draw time 2 (Amt (2)) is set to equal the residual hormone concentration (Amt(R)), wherein the value of Amt(R) is understood to be an estimate of the final residual hormone concentration. At step S118, the estimated residual concentration (Amt(R)) is used to determine T(1), which is the value of draw time 1 (D(1)) expressed in half life units. Equation 5 is used to determine this value.

$$T(X)=\log[(\text{Amt}(0)-\text{Amt}(R))/(\text{Amt}(1)-\text{Amt}(R))]/\log[2] \quad \text{Equation 5}$$

Equation 5 is calculated for X=1, corresponding to draw number 1 expressed in half-life units. At step S120 the value for draw number 2 is expressed in half-life units, using, for example, the value found for draw number 1 expressed in half-life units from Equation 5. Although other means may be used for determining the value of T(2), the efficient relationship $$T(2)=T(1)*D(2)/D(1) \quad \text{Equation 6}$$

is preferred. At this point in the method, the value of draw time 2 (D(2)) expressed in half-life units (T(2)) has been determined. Using T(2), the value for Amt(2)' is determined using Equation 2 at step S122. The expression Amt(2)' is the amount of hormone that would remain, theoretically, at draw time D(2) in the event that all glands which would secrete the hormone were excised. This value corresponds to column 4 in the example of Table 1, in which Equation 2 was also used.

The difference between the measured hormone concentration at draw time 2 (Amt(2)) and the theoretical concentration that would occur at draw time 2 if no residual remained (Amt(2)') is determined at step S124. This step obtains results similar to those retained in column 5 in the example of Table 1. After this difference is determined in step S124, the current estimate of the residual concentration (Amt(R)) is saved at step S127, and at step S129 a new estimate for the residual hormone concentration (Amt(R)) is determined using the difference found in step S124 and Equation 4. The method now has a better estimate for the residual concentration at draw time 2 than that which was initially used. At step S131 a difference or percent change between the old residual concentration estimate and the new residual concentration estimate is determined. As shown at step S135, the method branches back to step S118 if the difference or percent change between the old residual concentration estimate and the new residual concentration estimate is not within a predetermined range, and exits the loop to step S139 if the percentage change is within the predetermined range. At step S139 the current residual concentration value is output.

In addition to the residual concentration value, a graphical display of the decay curve of the hormone concentration of the patient is preferably also output on the display 34 (FIG. 1). Additionally, interpretive data for providing estimates and predictions on the amount of hormone-secreting tissue remaining in the patient, is preferably output. Predictions of residual hormone-secreting tissue can be made, based upon the residual hormone concentration value that is output by the method of the present invention. For example, if a patient has a normal configuration of 4 parathyroid hormone-secreting glands of normal size, and if the surgeon removes 1 gland resulting in an output by the method of the present invention of a residual value equal to 75% of the concentration at draw time 0 (Amt(0)), then the method of the present invention outputs an indication that 25% of the tissue has been removed. In a realistic scenario, however, the surgeon would be removing the single gland of the 4 glands more-than-likely because the single gland is hypersecreting. For example, the single hypersecreting gland may be emitting 75% of the hormone concentration at draw time 0, in which case the method of the present invention would indicate that the hypersecreting gland has not been removed unless the value of Amt(R) is ¼ the value of Amt(0). Other logical relationships between a patient's hormone-secreting tissues, the amount of tissue expected to be removed, and the resulting residual concentration can be used to provide analytical interpretive information to the surgeon. This interpretive information, relating information on the percentage of remaining hormone-secreting tissue, may very well be much more useful to the surgeon than the sole output of the predicted residual hormone concentration. For example, in the case of hypothyroid patients with diffused hyperplasia or multiple adenomas, a careful kinetic assessment of the PTH decay along with predetermined expected ranges for the PTH decay should be useful in recognizing the clinical entities, which are currently often misdiagnosed and inadequately treated.

Although exemplary embodiments of the invention have been shown and described, many other changes, modifications and substitutions, in addition to those set forth in the above paragraphs, may be made by one having ordinary skill in the art without necessarily departing from the spirit and scope of the present invention. For example, the hormone measuring equipment and assay described above are intended to be illustrative only, and other devices and procedures for detecting the presence of hormone concentrations, for example, are also contemplated by the present invention.

Also contemplated within the scope of the present invention are modified methods and apparatus embodiments for measuring other analyses such as, but not limited to, electrolytes, amino acids, amines, neurotransmitters, plasma proteins, glucose (and other sugars), lipids, endogenous substances and their metabolites, exogenous substances (radio-labeled and non radio-labeled) and their metabolites. Certain concentrations, for example, of these analyses may be indicative of a surgical success, partial success or non-success of removal of glandular tissues or hormone secreting tissues such as tumors or cancerous tissues; and the hormone secreted by these tissues may have long or short half-lifes. Moreover, the measurements of these analyses may serve as indirect measurements of certain levels of hormone or other substances, since some analyte concentrations and other concentrations (such as hormone) co-vary. Many or all of the advantages attributed to the hormone measuring methods and apparatus described herein are also intended and contemplated to be applicable to other non-hormone analyses such as, but not limited to, the above mentioned items and procedures, as would be known to one of ordinary skill in the art.

In accordance with another modified embodiment, instead of taking three draws from the same fluid compartment (i.e. all three draws from the plasma compartment) at three different time points, three draws for three different time points can be taken from two or more different fluid compartments. For example, the first draw can be taken from blood plasma compartment, the second draw can be taken from urine compartment, and the third draw can be taken from the third ventricle compartment in the brain of the patient. In accordance with another modified embodiment, the concentration measurements of hormone analyses and/or non-hormone analyses can be used to monitor the success, partial success or non-success of a removal of one or more non-glandular tissues, such as for example, kidney, heart, lung tissue, tumors and cancerous tissues.

Moreover, although the present invention is useful for monitoring the degree of success for surgical removal of tissues, another modified embodiment of the present invention may also be useful for monitoring the degree of success of surgical implantation of tissues. For example, Parkinsons' Disease patients suffer from a degeneration of the neuronal substantia nigra tissue. One current technique of treatment is to implant neuronal fetal substantia nigra tissue/cells into the corresponding region of the patient's brain as replacements. As these fetal tissue/cells attach to the patient's brain tissue, they become functional and produce L-Dopa and its metabolites. The present invention can be used to determine the success of the implantation, by measuring the brain third ventricle concentrations and kinetics of LDopa and its metabolites and comparing it to the expected and predicted kinetic profiles of L-Dopa in normal brains.

What is claimed is:

1. A method of using a computer processor to predict a residual hormone concentration in a patient after a removal of a portion of the patient's tissue which secretes the hormone, the method comprising the following steps:

(a) providing first, second and third measured hormone concentrations corresponding to first, second and third animal fluid samples taken from a patient at first, second and third sample times, respectively;

(b) assigning an estimated value to the residual hormone concentration of the patient that is to be predicted;

(c) determining an expression in half lifes of the second sample time, using the estimated value of step (b);

(d) determining an expression in half lifes of the third sample time, using the determined expression in half lifes of the second sample time of step (c) and a ratio of the third sample time and the second sample time;

(e) determining a hormone concentration that would remain at the second sample time if the residual hormone concentration were zero, using the determined expression in half lifes of the second sample time;

(f) calculating a difference between the determined hormone concentration and the third measured hormone concentration;

(g) remembering the estimated value for the residual hormone concentration as an old estimated value;

(h) finding a new estimated value for the residual hormone concentration, using the calculated difference of step (f);

(i) repeating steps (c) through (g) until a difference or percent change between the old estimated value and the new estimated value reaches a predetermined value; and (j) outputting the new estimated value of step (I) as the predicted residual hormone concentration.

2. The method as set forth in claim 1, wherein the providing step comprises a step of inputting first, second and third measured hormone concentrations corresponding to first, second and third animal fluid samples taken from a patient at first, second and third sample times, respectively.

3. The method as set forth in claim 2, wherein the providing step comprises a step of inputting, via a keyboard, data relating to the first, second and third measured hormone concentrations to the computer processor.

4. The method as set forth in claim 1, wherein the providing step comprises a step of physically placing the first, second and third animal fluid samples into an apparatus which is coupled to the computer processor.

5. The method as set forth in claim 4, wherein the providing step comprises a step of physically placing first, second and third Ethylenediaminetetraacetic Acid (EDTA) treated animal fluid samples into the apparatus as the first, second and third samples.

6. The method as set forth in claim 5, wherein the apparatus and the computer processor determine the first, second and third measured hormone concentrations from the first, second and third animal fluid samples.

7. The method as set forth in claim 6, wherein:

the step of physically placing first, second and third animal fluid samples into an apparatus comprises a step of a user physically placing the first, second and third animal fluid samples into the apparatus; and the step of the apparatus and the computer processor determining the first, second and third measured hormone concentrations from the first, second and third animal fluid samples is performed automatically.

8. The method as set forth in claim 1, wherein the step of assigning an estimated value to the residual hormone concentration of the patient that is to be predicted, comprises a step of using the third animal fluid sample as the estimated value.

9. The method as set forth in claim 1, wherein the first hormone concentration of the 3 hormone concentrations corresponds to a baseline hormone concentration, which corresponds to a baseline animal fluid sample that was taken from the patient at a time before the removal of the portion of the patient's glandular tissue.

10. The method as set forth in claim 1, wherein the step of outputting the new estimated value as the predicted residual hormone concentration includes a step of outputting a graphical display of a decay curve of the hormone concentration of the patient.

11. The method as set forth in claim 1, wherein the step of providing first, second and third measured hormone concentrations comprises a step of providing first, second and third measured concentrations of parathyroid hormone (PTH).

12. The method as set forth in claim 1, wherein the computer processor is used to predict a residual hormone concentration in a patient after removal of a portion of the patient's glandular tissue which secretes the hormone.

13. The method as set forth in claim 1, wherein the step providing first, second and third measured hormone concentrations comprises a step of providing first, second, and third measured hormone concentrations corresponding to first, second, and third human fluid samples taken from a patient at first, second, and third sample times, respectively.

14. The method as set forth in claim 1, wherein the step of providing first, second and third measured hormone concentrations comprises a step of providing first, second, and third measured hormone concentrations corresponding to first, second, and third human fluid samples taken from a patient at first, second, and third sample times, respectively, at least one of the first, second and third measured hormone concentrations belonging to a different fluid compartment than the other two.

15. A method of using a computer processor to predict a residual substance concentration in a patient after a removal of a portion of the patient's tissue, the method comprising the following steps:

(a) providing a plurality of measured substance concentrations corresponding to a plurality of animal fluid samples taken from a patient at a plurality of sample times, respectively; and (b) iteratively calculating a residual substance concentration, by successively approximating specific values for the residual substance concentration and a half-life, until a predetermined condition is met, to thereby predict the residual substance concentration in the patient.

16. The method as set forth in claim 15, wherein the step of iteratively calculating the residual substance concentration is followed by a step of outputting the iteratively-calculated residual substance concentration as the predicted residual substance concentration.

17. The method as set forth in claim 15, wherein the step of iteratively calculating the residual substance concentration comprises a step of iteratively calculating both the residual substance concentration and a half-life value of the substance concentration in the patient.

18. The method as set forth in claim 15, wherein the computer processor is used to predict a residual hormone concentration in a patient after removal of a portion of the patient's glandular tissue which secretes the hormone.

19. The method as set forth in claim 18, wherein the step of iteratively calculating the residual substance concentration is followed by a step of outputting data that represents a residual amount of glandular tissue that will remain in the patient after the removal of the portion of the patient's glandular tissue.

20. The method as set forth in claim 15, wherein the step of iteratively calculating the residual substance concentration is followed by a step of outputting data that represents a residual amount of glandular tissue that will remain in the patient after the removal of the portion of the patient's glandular tissue.

21. The method as set forth in claim 15, wherein the step of providing a plurality of measured substance concentrations comprises a step of providing more than 3 measured substance concentrations corresponding to more than 3 animal fluid samples taken from a patient at more than 3 sample times, respectively.

22. The method as set forth in claim 15, wherein the step of providing a plurality of measured substance concentrations comprises a step of providing at least 3 measured substance concentrations corresponding to at least 3 animal fluid samples taken from a patient at at least 3 sample times, respectively.

23. The method as set forth in claim 15, wherein the step of iteratively calculating the residual substance concentration comprises a step of iteratively calculating both the residual substance concentration and a half-life value of the substance concentration in the patient, using the at least 3 measured substance concentrations and the at least 3 sample times.

24. The method as set forth in claim 22, wherein the providing step comprises a step of physically placing at least 3 animal fluid samples into an apparatus.

25. The method as set forth in claim 24, wherein the apparatus and the computer processor determine the at least 3 measured substance concentrations from the at least 3 animal fluid samples.

26. The method as set forth in claim 19, wherein the providing step comprises a step of physically placing at least 3 Ethylenediaminetetraacetic Acid (EDTA) treated animal plasma samples into an apparatus as the at least 3 animal fluid samples.

27. The method as set forth in claim 20, wherein:
the step of physically placing at least 3 animal fluid samples into an apparatus comprises a step of a user physically placing the at least 3 animal fluid samples into the apparatus; and
the step of the apparatus and the computer processor determining the at least 3 measured substance concentrations from the at least 3 animal fluid samples is performed automatically.

28. The method as set forth in claim 15, wherein the step of iteratively calculating a residual substance concentration is followed by a step of outputting the iteratively-calculated residual substance concentration as the predicted residual substance concentration.

29. The method as set forth in claim 28, wherein the step of outputting the predicted residual substance concentration includes a step of outputting a graphical display of a decay curve of the substance concentration of the patient.

30. The method as set forth in claim 15, wherein the step of providing a plurality of measured substance concentrations comprises a step of providing a plurality of measured concentrations of parathyroid hormone (PTH).

31. The method as set forth in claim 15, wherein the steps of providing a plurality of measured substance concentrations comprises a step of providing a plurality of measured substance concentrations corresponding to a plurality of human fluid samples taken from a patient at a plurality of sample times, respectively.

32. A method of using a computer processor to predict a residual amount of tissue remaining in a patient after a removal of a portion of the tissue, the tissue when in the patient secreting a hormone, the method comprising the following steps:

(a) providing first, second and third measured hormone concentrations corresponding to first, second and third animal fluid samples taken from a patient at first, second and third sample times, respectively;

(b) assigning an estimated value to a residual hormone concentration of the patient that is to be predicted;

(c) determining an expression in half lifes of the second sample time, using the estimated value of step (b);

(d) determining an expression in half lifes of the third sample time, using the determined expression in half lifes of the second sample time of step (c) and a ratio of the of the third sample time and the second sample time;

(e) determining a hormone concentration that would remain at the third sample time if the residual hormone concentration were zero, using the determined expression in half lifes of the third sample time;

(f) calculating a difference between the determined hormone concentration and the third measured hormone concentration;

(g) remembering the estimated value for the residual hormone concentration as an old estimated value;

(h) finding a new estimated value for the residual hormone concentration, using the calculated difference of step (f);

(i) repeat steps (c) through (h) until a difference or percent change between the old estimated value and the new estimated value reaches a predetermined value; and (j) outputting data that represents a residual amount of tissue that remains in the patient after the removal of the portion of the tissue.

33. The method as set forth in claim 32, wherein the providing step comprises a step of inputting first, second and third measured hormone concentrations corresponding to first, second and third animal fluid samples taken from a patient at first, second and third sample times, respectively.

34. The method as set forth in claim 32, wherein the providing step is proceeded by a step of physically placing first, second and third Ethylenediaminetetraacetic Acid (EDTA) treated animal plasma samples into the apparatus as the first, second and third animal fluid samples, respectively.

35. The method as set forth in claim 34, wherein:
the apparatus and the computer processor determine the first, second and third measured hormone concentrations from the first, second and third animal fluid samples;
the step of physically placing first, second and third animal fluid samples into an apparatus comprises a step of a user physically placing the first, second and third animal fluid samples into the apparatus; and
the step of the apparatus and the computer processor determining the first, second and third measured hormone concentrations from the first, second and third animal fluid samples includes a step of the apparatus and the computer processor automatically determining the first, second and third measured hormone concentrations from the first, second and third animal fluid samples.

36. The method as set forth in claim 32, wherein the step of providing first, second and third measured hormone concentrations comprises a step of inputting, via a keyboard, data relating to the first, second and third measured hormone concentrations to the computer processor.

37. The method as set forth in claim 32, wherein:
the first hormone concentration of the 3 hormone concentrations corresponds to a baseline hormone concentration, which corresponds to a baseline animal fluid sample that was taken from the patient at a time before a surgical removal of a portion of the glandular tissue of the patient; and the step of assigning an estimated value to the residual hormone concentration of the patient that is to be predicted, comprises a step of using the third animal fluid sample as the estimated value.

38. The method as set forth in claim 32, wherein the step of providing first, second and third measured hormone concentrations comprises a step of providing first, second and third measured concentrations of parathyroid hormone (PTH).

39. The method as set forth in claim 32, wherein the steps of providing first, second, and third measured hormone concentrations comprises a step of providing first, second and third measured hormone concentrations corresponding to first, second and third human fluid samples taken from a patient at first, second and third sample times, respectively.

40. The method as set forth in claim 32, wherein the step of providing first, second and third measured hormone concentrations comprises a step of providing first, second, and third measured hormone concentrations corresponding to first, second, and third human fluid samples taken from a patient at first, second, and third sample times, respectively, at least one of the first, second and third measured hormone concentrations belonging to a different fluid compartment than the other two.

41. A method of using a computer processor to predict a residual hormone concentration in a patient after a removal of a portion of the patient's tissue which secretes the hormone, the method comprising the following steps:

(a) providing first, second and third measured hormone concentrations corresponding to first, second and third animal fluid samples taken from a patient at first, second and third sample times, respectively;

(b) assigning an estimated value to the residual hormone concentration of the patient that is to be predicted;

(c) determining an expression in half lifes of the second sample time, using the estimated value of step (b);

(d) determining a hormone concentration that would remain at the second sample time if the residual hormone concentration were zero, using the determined expression in half lifes of the second sample time of step (c);

(e) calculating a difference between the determined hormone concentration and the third measured hormone concentration;

(f) remembering the estimated value for the residual hormone concentration as an old estimated value;

(g) finding a new estimated value for the residual hormone concentration, using the calculated difference of step (e); and (h) repeating steps (c) through (g) until a difference or percent change between the old estimated value and the new estimated value reaches a predetermined value.

42. The method as set forth in claim 41, wherein the computer processor is used to predict a residual hormone concentration in a patient after removal of a portion of the patient's glandular tissue which secretes the hormone.

43. The method as set forth in claim 41, wherein the step of providing first, second and third measured hormone concentrations comprises a step of providing first, second and third measured hormone concentrations corresponding to first, second and third human fluid samples taken from a patient at first, second and third sample times, respectively.

44. The method as set forth in claim 41, wherein the step of providing first, second and third measured hormone concentrations comprises a step of providing first, second, and third measured hormone concentrations corresponding to first, second, and third human fluid samples taken from a patient at first, second, and third sample times, respectively, at least one of the first, second and third measured hormone concentrations belonging to a different fluid compartment than the other two.

45. An apparatus for predicting a residual hormone concentration in a patient after a removal of a portion of the patient's tissue which secretes the hormone, comprising:

(a) an input device constructed to receive a plurality of measured hormone concentrations corresponding to a plurality of animal fluid samples taken from a patient at a plurality of sample times, respectively; and (b) a computer processor configured to iteratively calculate a residual hormone concentration, by successively approximating specific values for the residual hormone concentration and a half-life, until a predetermined condition is met, to thereby predict the residual hormone concentration in the patient.

46. The apparatus as set forth in claim 45, wherein the input device is constructed to receive a plurality of measured concentrations of parathyroid hormone (PTH).

47. The apparatus as set forth in claim 45, wherein:

the computer processor is further configured to generate data denoting a residual amount of tissue that will remain in the patient after the removal of the portion of the patient's tissue; and the apparatus further comprises an output device constructed to output the generated data denoting the residual amount of tissue.

48. The apparatus as set forth in claim 45, wherein the computer processor is further configured to iteratively calculate a half-life value of the hormone concentration in the patient.

49. The apparatus as set forth in claim 45, wherein the plurality of measured hormone concentrations comprises at least 3 measured hormone concentrations corresponding to at least 3 animal fluid samples taken from a patient at at least 3 sample times, respectively.

50. The apparatus as set forth in claim 49, wherein the computer processor is configured to iteratively calculate both the residual hormone concentration and a half-life value of the hormone concentration in the patient, using the at least 3 measured hormone concentrations and the at least 3 sample times.

51. The apparatus as set forth in claim 45, wherein the plurality of measured hormone concentrations comprises more than 3 measured hormone concentrations corresponding to more than 3 animal fluid samples taken from a patient at more than 3 sample times, respectively.

52. The apparatus as set forth in claim 45, wherein:

the input device is constructed to receive the plurality of animal fluid samples; and the computer processor is configured to automatically determine the plurality of measured hormone concentrations from the plurality of animal fluid samples.

53. The apparatus as set forth in claim 52, wherein each animal fluid sample comprises Ethylenediaminetetraacetic Acid (EDTA) treated animal plasma.

54. The apparatus as set forth in claim 45, wherein the input device comprises a keyboard.

55. The apparatus as set forth in claim 54, wherein:

the apparatus further comprises an output device; and the computer processor is configured to instruct the output device to output the iteratively-calculated residual hormone concentration as the predicted residual hormone concentration.

56. The apparatus as set forth in claim 54, wherein the computer processor is further configured to generate information relating to a decay curve of the hormone concentration of the patient, and is configured to instruct the output device to output a graphical display of a decay curve of the hormone concentration of the patient.

57. The apparatus as set forth in claim 45, wherein the input device is constructed to receive a plurality of measured hormone concentrations corresponding to a plurality of human fluid samples taken from a patient at a plurality of sample times, respectively.

58. The apparatus as set forth in claim 45, wherein the apparatus predicts a residual hormone concentration in a patient after removal of a portion of the patient's glandular tissue.

59. The apparatus as set forth in claim 45, wherein the computer processor is disposed remotely from this user input device and is coupled to the user input device through a computer network.

60. A system for predicting a residual hormone concentration comprising the apparatus of claim 45, and further comprising an immuno-assay to determine the plurality of the measured hormone concentrations.

61. The system as set forth in claim 60, and further comprising a vibrating heat block.

62. An apparatus for predicting a residual hormone concentration in a patient after a removal of a portion of the patient's tissue which secretes the hormone, comprising:

(a) an input device constructed to receive a plurality of measured hormone concentrations corresponding to a plurality of animal fluid samples taken from a patient at a plurality of sample times, respectively; and (b) a computer processor configured to iteratively calculate a residual amount of tissue, which will remain in the patient after the removal of the portion of the patient's tissue, by successively approximating specific values for the residual hormone concentration and a half-life, until a predetermined condition is met, to thereby predict the residual hormone concentration in the patient.

63. The apparatus as set forth in claim 62, wherein the input device is constructed to receive a plurality of measured concentrations of parathyroid hormone (PTH).

64. The apparatus as set forth in claim 62, wherein the apparatus further comprises an output device constructed to output the generated data denoting the residual amount of tissue.

65. The apparatus as set forth in claim 62, wherein the computer processor is further configured to iteratively calculate a half-life value of the hormone concentration in the patient.

66. The apparatus as set forth in claim 62, wherein the plurality of measured hormone concentrations comprises at least 3 measured hormone concentrations corresponding to at least 3 animal fluid samples taken from a patient at at least 3 sample times, respectively.

67. The apparatus as set forth in claim 66, wherein the computer processor is configured to iteratively calculate both the residual amount of tissue and a half-life value of the hormone concentration in the patient, using the at least 3 measured hormone concentrations and the at least 3 sample times.

68. The apparatus as set forth in claim 62, wherein the plurality of measured hormone concentrations comprises more than 3 measured hormone concentrations corresponding to more than 3 animal fluid samples taken from a patient at more than 3 sample times, respectively.

69. The apparatus as set forth in claim 62, wherein:

the input device is constructed to receive the plurality of animal fluid samples; and the computer processor is configured to automatically determine the plurality of measured hormone concentrations from the plurality of animal fluid samples.

70. The apparatus as set forth in claim 69, wherein each animal fluid sample comprises Ethylenediaminetetraacetic Acid (EDTA) treated animal plasma.

71. The apparatus as set forth in claim 62, wherein the input device comprises a keyboard.

72. The apparatus as set forth in claim 71, wherein:

the apparatus further comprises an output device; and the computer processor is configured to instruct the output device to output the iteratively-calculated residual amount of tissue as the predicted residual amount of tissue.

73. The apparatus as set forth in claim 71, wherein the computer processor is further configured to generate information relating to a decay curve of the hormone concentration of the patient, and is configured to instruct the output device to output a graphical display of a decay curve of the hormone concentration of the patient.

74. The apparatus as set forth in claim 62, wherein the input device is constructed to receive a plurality of measured hormone concentrations corresponding to a plurality of human fluid samples taken from a patient at a plurality of sample times, respectively.

75. The apparatus as set forth in claim 62, wherein the apparatus predicts a residual amount of tissue in a patient after removal of a portion of the patient's glandular tissue.

76. The apparatus as set forth in claim 62, wherein the computer processor is disposed remotely from this user input device and is coupled to the user input device through a computer network.

77. A system for predicting a residual amount of tissue comprising the apparatus of claim 62, and further comprising an immuno-assay to determine the plurality of the measured hormone concentrations.

78. The system as set forth in claim 77, and further comprising a vibrating heat block.

* * * * *

UNITED STATES PATENT AND TRADEMARK OFFICE
CERTIFICATE OF CORRECTION

PATENT NO. : 6,154,706
DATED : November 28, 2000
INVENTOR(S) : Remaley et al.

Page 1 of 1

It is certified that error appears in the above-identified patent and that said Letters Patent is hereby corrected as shown below:

Column 9,
Line 59, delete "$Amt(X)-Amt(X)'=Amt(R)*(2^{T(X)}-1)/(2_{T(X)})$" and insert
-- $Amt(X)-Amt(X)'=Amt(R) * (2^{T(X)}-1)/(2^{T(X)})$ --
Line 64, delete "$2_{T(X)}-1$" and insert -- $2^{T(X)}-1$ --
Line 65, delete "$2_{T(X)}$" and insert -- $2^{T(X)}$ --

Column 10,
Line 9, delete "$Amt(R)=[Amt(X)-Amt(X)']*2_{T(X)}/(2_{T(X)}-1)$" and insert
-- $Amt(R)=[Amt(X)-Amt(X)']*2^{T(X)}/(2^{T(X)}-1)$ --

Signed and Sealed this

Sixteenth Day of April, 2002

Attest:

JAMES E. ROGAN
*Director of the United States Patent and Trademark Office*

*Attesting Officer*